United States Patent [19]
Callis et al.

[11] Patent Number: 5,341,691
[45] Date of Patent: Aug. 30, 1994

[54] DUAL USE PRESSURIZED AND UNPRESSURIZED OIL SAMPLING APPARATUS

[76] Inventors: Rex D. Callis, 2904 Hamburg Pike, Jeffersonville, Ind. 47130; John M. Callis, 7713 Old Hwy. 60, Sellersburg, both of Ind. 47172

[21] Appl. No.: 860,145

[22] Filed: Mar. 31, 1992

[51] Int. Cl.$^5$ .............................................. G01N 1/14
[52] U.S. Cl. ................... 73/863.83; 73/864.34; 73/863.814; 73/864.35; 73/864.51
[58] Field of Search ........... 73/864.34, 864.35, 863.83, 73/863.84, 863.81, 864.63, 864.51; 141/27, 130; 222/152, 204

[56] References Cited

U.S. PATENT DOCUMENTS

| | | | |
|---|---|---|---|
| 3,442,136 | 5/1969 | Wilson, Jr. ................... | 73/864.34 |
| 4,051,731 | 10/1977 | Bohl et al. ........................ | 73/863.33 |
| 4,289,027 | 9/1981 | Gleaves ............................ | 73/863.86 |
| 4,524,811 | 6/1985 | Taylor ............................... | 73/863.81 |
| 4,548,088 | 10/1985 | Hood ................................ | 73/864.34 |
| 4,549,440 | 10/1985 | Fournier et al. ................. | 73/863.85 |
| 4,580,453 | 4/1986 | Taylor ............................... | 73/863.86 |
| 4,930,360 | 6/1990 | Tan ................................... | 73/864.34 |
| 5,193,404 | 3/1993 | Tan ................................... | 73/864.34 |

Primary Examiner—Hezrone E. Williams
Assistant Examiner—Nashmiya N. Ashraf
Attorney, Agent, or Firm—Locke Reynolds

[57] ABSTRACT

An oil sampling apparatus for taking samples from either pressurized or non-pressurized oil sources is provided. The oil sampling apparatus includes a body configured to define a conduit therethrough, a vacuum passageway defined to extend through the body in fluid communication with the conduit, and a pressurized oil passageway defined to extend through the body in fluid communication with the conduit. The body further defines a rigid tube having a tube interior connectable between a source of pressurized oil and the pressurized oil passageway. A sample bottle is positionable adjacent to the body in fluid tight communication with the conduit and a manually operated vacuum pump is attached in fluid communication to the vacuum passageway to allow oil to be drawn from a non-pressurized oil source, through the conduit, and into the sample bottle. Oil from pressurized sources can be collected by allowing a needle positioned in the tube interior to trigger release of pressurized oil from the source of pressurized oil when connected to the source of pressurized oil.

19 Claims, 5 Drawing Sheets

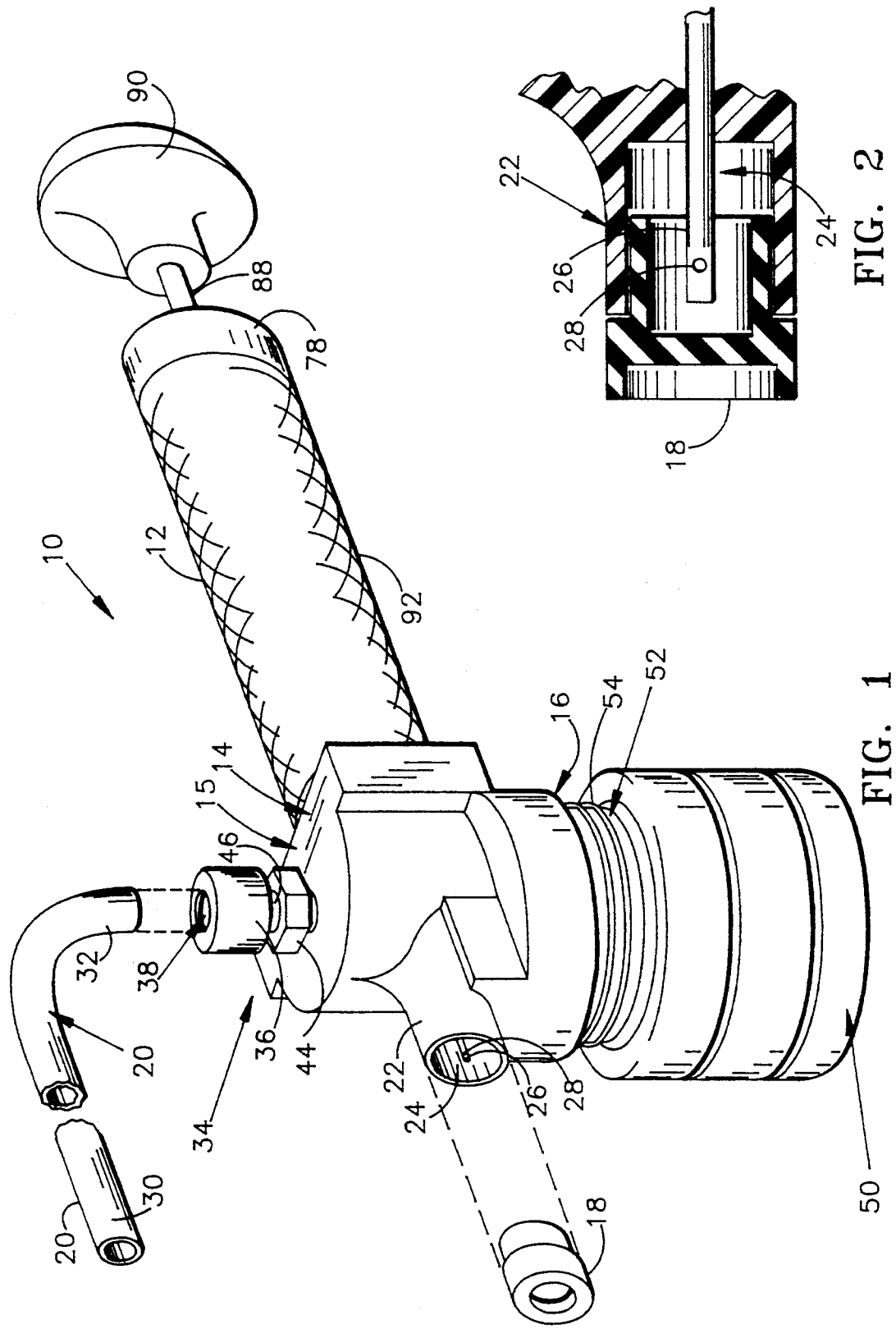

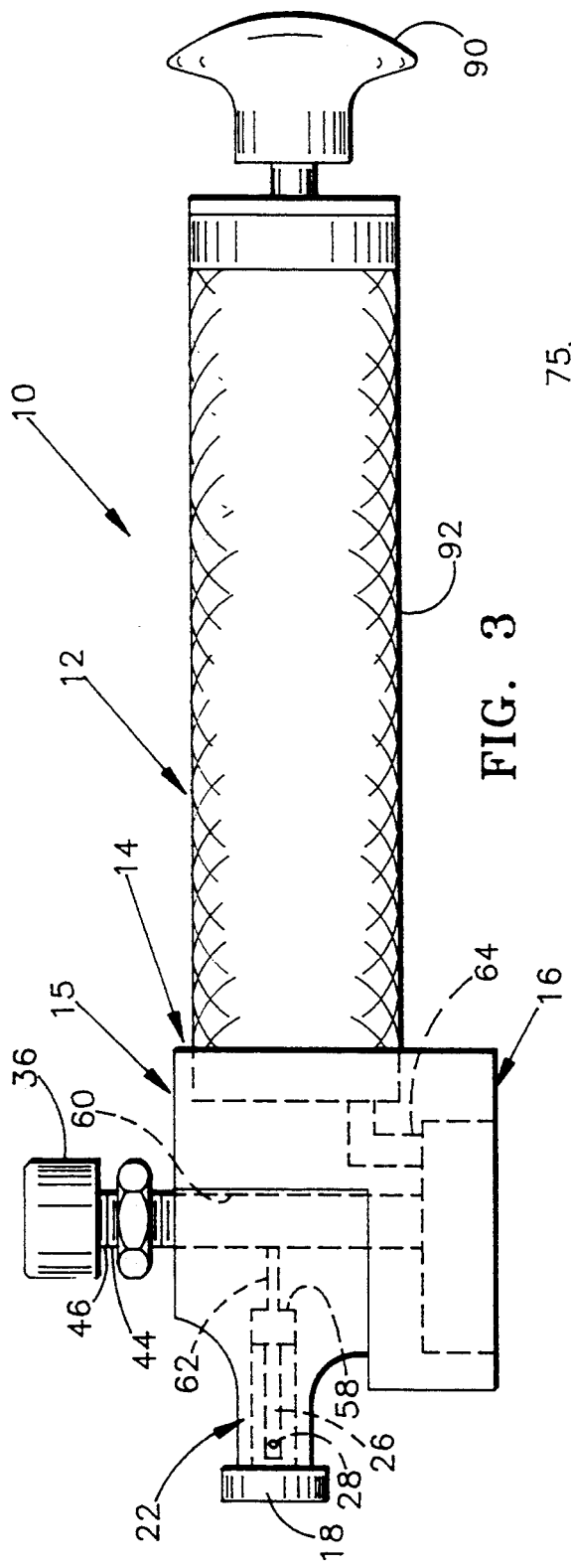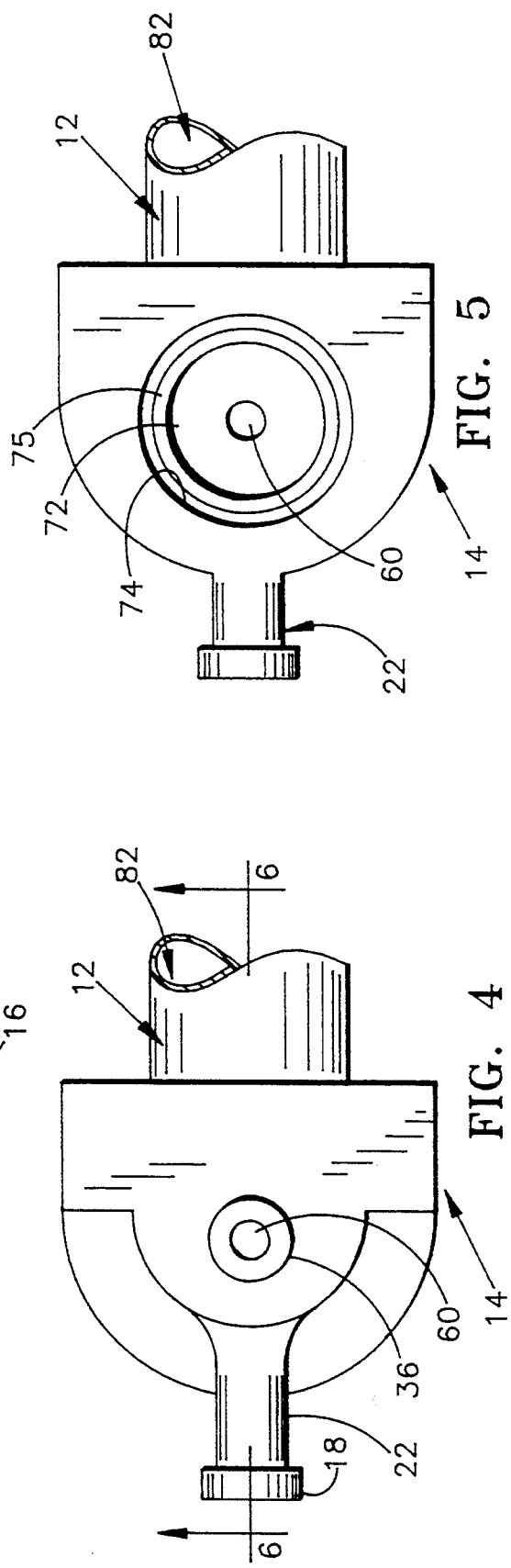

DUAL USE PRESSURIZED AND UNPRESSURIZED OIL SAMPLING APPARATUS

BACKGROUND AND SUMMARY OF THE INVENTION

The present invention relates to manually operated oil sampling equipment for retrieval of oil samples from industrial machinery. More particularly, the present invention relates to dual function oil sampling equipment able to retrieve and store oil samples from either a pressurized oil source or a non-pressurized oil source.

Large industrial vehicles are commonly used in the transportation, construction, or mining industries. Such vehicles require large amounts of lubricating oils to reduce friction of moving engine parts and maintain seals. Periodic replacement of the lubricating oil is necessary because the lubricating oil carbonizes (oil breakdown), changing its viscosity and other lubrication properties. In addition, periodic lubricating oil changes are desirable because the lubricating oil may become contaminated with foreign particles such as metal shavings from engine parts, greatly increasing engine wear.

However, given the high cost of lubricating oil, the difficulties in disposal of waste oil, and the substantial maintenance time required for lubricating oil changes, it is highly desirable to maximize the time between lubricating oil changes. Simply setting periodic times for lubricating oil changes may permit unnecessary engine wear if the lubricating oil is contaminated before a scheduled oil change, or waste time and money if the oil is still usable at the time of the scheduled oil change. One method for ensuring that lubricating oil in industrial machinery is only replaced when necessary involves a program of lubricating oil sample retrieval. (See, for example, U.S. Pat. No. 4,548,088 which describes an oil sampling system). An oil sample is periodically taken, analyzed, and based on that analysis a complete lubricating oil change may be ordered. With this program, oil is only replaced when required, not when determined by an inflexible schedule.

In accordance with the present invention, an oil sampling apparatus suitable for periodic retrieval of lubricating oil samples is provided. The oil sampling apparatus of the present invention is designed to accommodate withdrawal of an oil sample from a pressurized oil source (for example, an idling internal combustion engine) or can alternatively be used to manually pump an oil sample from an unpressurized oil source. The apparatus includes a body having an upper and a lower side, the body being configured to define a conduit therethrough extending between the upper and lower sides. Both a vacuum passageway and a pressurized oil passageway are defined to extend through the body in fluid communication with the conduit. The body further defines a rigid tube having a tube interior connectable between a source of pressurized oil and the pressurized oil passageway.

A sample bottle, typically disposable, for accepting, holding, and storing an oil sample is positionable adjacent to the lower side of the body in fluid tight communication with the conduit. A manually operated vacuum pump is attached in fluid communication to the vacuum passageway, and a needle is positioned in the tube interior. The needle is configured to trigger release of pressurized oil from the source of pressurized oil when pushed into mating configuration with the source of pressurized oil.

A flexible tube is also provided for attachment to a non-pressurized source of oil. The flexible tube is insertible through the upper side of the body into the conduit for conveying oil between a non-pressurized oil source and the conduit, and a coupling system is attached to the upper side of the body to connect the flexible tube in fluid tight connection with the conduit. To prevent intake of atmospheric air into the conduit during operation of the manually operated vacuum pump, a removable seal for removably sealing the tube interior is provided. When the oil sampling apparatus is used for withdrawing non-pressurized oil samples, the tube and tube interior is closed off. This promotes the ability of an operator to draw a vacuum in the conduit, and consequently eases the task of drawing thick and viscous oil from a non-pressurized oil source through the flexible tubing and conduit, for storage in the sample bottle.

In an alternative embodiment, an oil sampling apparatus for taking an oil sample from either a pressurized or non-pressurized oil source and storing the oil sample in a removably attached sample bottle includes a body formed to define a conduit therethrough. The body further defines a vacuum passageway therethrough in fluid communication with the conduit and a pressurized oil passageway is defined to extend through the body in fluid communication with the conduit.

A mechanism for attaching a sample bottle to the body in fluid communication with the conduit is provided. A manually operated vacuum pump is attached in fluid communication to the vacuum passageway and a triggering release mechanism is provided for release of pressurized oil from a pressurized oil source when the triggering mechanism is in fluid communication with the pressurized oil passageway and a source of pressurized oil.

In addition to releasing pressurized oil, the apparatus of the present invention can recover non-pressurized oil. A mechanism for conveying oil between a non-pressurized oil source and the conduit is provided, along with a mechanism for coupling the conveying mechanism in fluid tight connection with the conduit. In operation, the pressurized oil passageway is sealed to promote drawing a vacuum in the conduit when oil is drawn by action of the manually operated vacuum pump from a non-pressurized oil source through the conveying mechanism into the conduit.

Typically, the triggering mechanism includes a rigid tube integrally defined to project from the body, the rigid tube having a tube interior connectable between a source of pressurized oil and the pressurized oil passageway. A needle is positioned in the tube interior, the needle being configured to trigger release of pressurized oil from the source of pressurized oil when connected to the source of pressurized oil. The needle may be formed to define a needle hole therethrough, the needle hole being connected in fluid communication with the pressurized oil passageway to allow passage of pressurized oil from the tube interior, through the needle hole, and into the pressurized oil passageway.

In a most preferred embodiment, the conveying mechanism includes a flexible tube having a proximal end positioned to extend into the conduit and a distal end positionable in fluid communication with a non-pressurized oil source. In this embodiment, the coupling mechanism may be include a stem attached to the body in fluid communication with the conduit, the stem extending outward from the body and allowing insertion therethrough of the flexible tube. A compression nut having a passageway therethrough to allow insertion therethrough of the flexible tube is also provided, with attachment of the compression nut to the stem compressing a compressible elastic washer positioned therebetween to hold the flexible tube in sealing engagment with the stem.

The present invention may be best understood by consideration of the following preferred embodiments and drawings, which present the best mode of practicing the invention as presently perceived.

BRIEF DESCRIPTION OF THE DRAWINGS

FIG. 1 is an exploded perspective view of an oil sampling apparatus, illustrating a body connected to a manually operated vacuum pump, the body having an upper side that supports attachment of a coupling system for fluid tight attachment of a flexible tube suitable for withdrawing oil from non-pressurized oil sources, and the body further defining a rigid tube accomodating a needle that triggers release of oil from pressurized oil sources, with oil entering from either the rigid tube or flexible tube and passing through the body into a sample bottle attached to the lower side of the body;

FIG. 2 is a cross-sectional view of the rigid tube blocked by an inserted plug;

FIG. 3 is a side view of the oil sampling apparatus illustrated in FIG. 1;

FIG. 4 is a top view of the oil sampling apparatus illustrated in FIG. 3, the vacuum pump being broken away to emphasize the upper side of the body;

FIG. 5 is a bottom view of the oil sampling apparatus illustrated in FIG. 3, the vacuum pump being broken away to emphasize the lower side of the body;

DETAILED DESCRIPTION OF THE DRAWINGS

Figure 6:
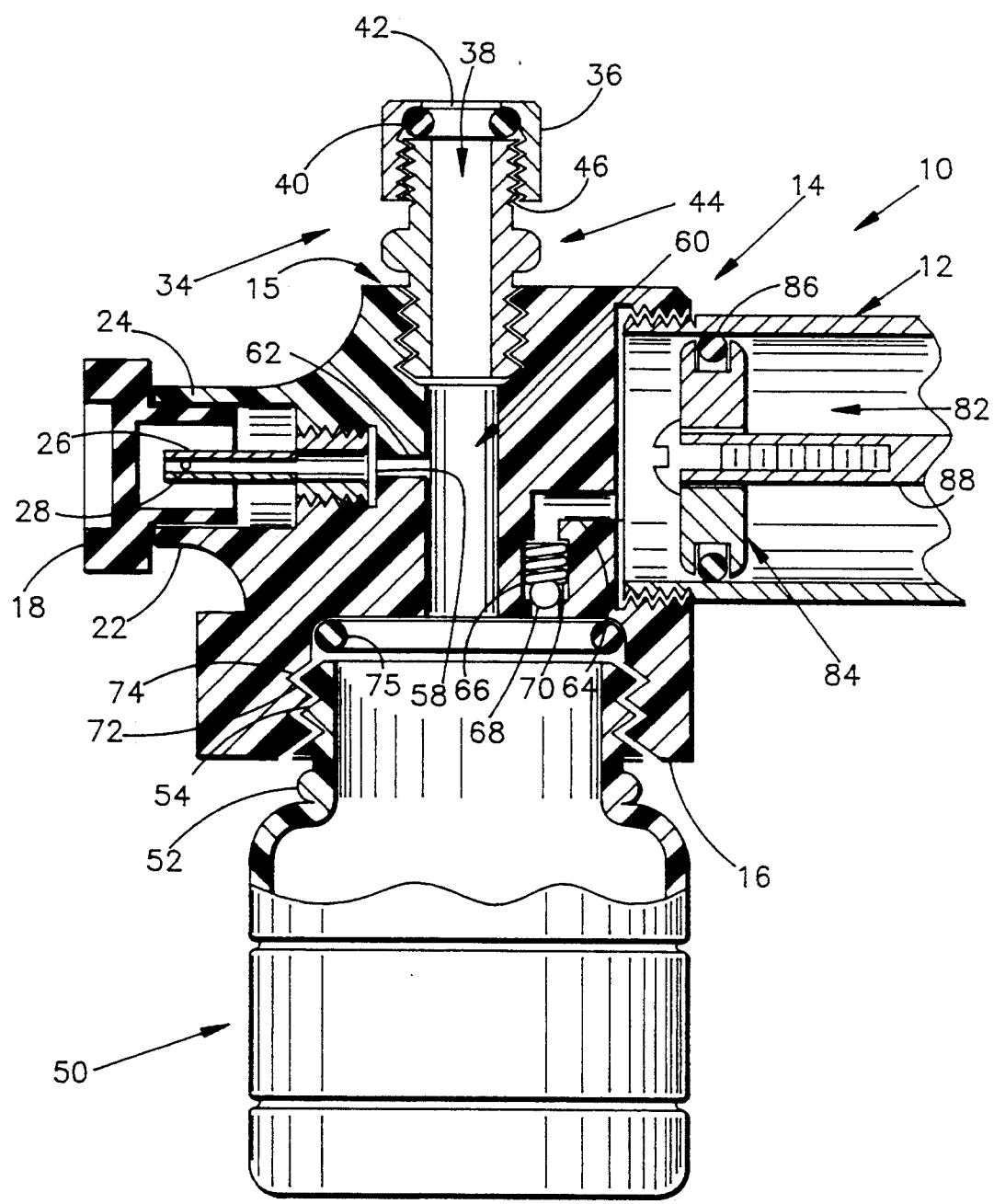
FIG. 6 is a cross-sectional view taken along line 6-6 of the oil sampling apparatus as illustrated in FIG. 4, with a conduit passing through the body between its upper and lower sides being shown, as well as a pressurized oil passageway and a vacuum passageway being respectively connected in fluid communication with the conduit.

A dual purpose oil sampling apparatus 10 is illustrated in FIGS. 1 through 6. An exploded perspective view of the dual purpose oil sampling apparatus 10 is shown in FIG. 1. The apparatus 10 can be used to withdraw and collect oil samples from both non-pressurized and pressurized oil sources. The oil sampling apparatus 10 includes a body 14 having an upper side 15 and an oppositely situated lower side 16. The body 14 is connected to a manually operated vacuum pump 12. The upper side 15 of the body 14 supports attachment of a coupling system 34 for fluid tight attachment of a flexible tube 20 suitable for withdrawing oil from non-pressurized oil sources. The flexible tube 20 has a distal end 30 for insertion into a non-pressurized oil source (not shown) and a proximal end 32 that can be held by the coupling system 34. Lubricating oil drawn through the flexible tube 20 in response to application of a vacuum by the vacuum pump 12 passes through a conduit 60 defined in the body 12 and is collected in a sample bottle 50 maintained in fluid communication with the conduit 60.

In addition to accommodating withdrawal of lubricating oil from non-pressurized oil sources, the body 14 is formed to integrally define a rigid tube 22 that allows collection of oil samples derived from pressurized oil sources (not shown). When not in use, this tube is typically sealed with an airtight plug 18, best indicated in cross section in FIG. 2, or other type of sealing cap, membrane, or wall. The plug 18 is typically formed from a resilient, durable, and airtight polymeric material, and is tapered to enhance sealing effectiveness when inserted into tube interior 24 of the tube 22.

Tube interior 24 of the rigid tube 22 accommodates a needle 26 held in a seat 58 defined by the body 14. The needle 26 is configured to trigger release of oil from pressurized oil sources when it is positioned in sealed contact with the pressurized oil source. Of course, alternative embodiments in which a semi-flexible tube or other sealing mechanism for enclosing a needle or other type triggering mechanism are also contemplated.

The needle 26 is provided with a central channel (not shown) accessible through a needle hole 28 defined in the needle 26 to allow pressurized oil to pass through the needle 26 into a pressurized oil passageway 62 defined in the body 14. The pressurized oil passageway is defined in fluid communication with the conduit 60. Oil enters tube interior 24 of the rigid tube 22 and passes through the body 14 into the sample bottle 50 attached to the lower side 16 of the body 14.

As will be appreciated by those skilled in the art, the configuration of the needle can be modified to allow release of differing types of pressurized oil triggers. In addition, the needle is not required to have a central channel for conveying pressurized oil, but can be, for example, a solid pin, a mounted rod, projection, or arm that triggers release of oil directly into the pressurized oil passageway.

Typically, the body 14 of the oil sampling apparatus 10 is mold formed from a high density polyethylene or other commonly available and durable polymer, although of course other materials may be used (e.g., cast and machined aluminum). The body 14 can be integrally formed, or may alternatively be assembled from multiple pieces. The body 14 defines conduit 60 (best seen in FIGS. 3 and 6) which extends between the upper side 15 and lower side 16 of the body 14. The conduit 60 is connected at its upper side 15 to a stem 44 of the coupling system 34, with the stem 44 being threadably inserted partially into the conduit 60. At its lower side 16, the conduit 60 opens into a neck receptacle 72 fitted with internal threads 74 and a sealing ring 75 to engage and hold in sealed fluid communication a sample bottle 50.

As best shown in FIGS. 3 and 6, the conduit 60 defined in the body 14 is connected in fluid communication with the vacuum pump 12 by a vacuum passageway 64 defined by the body 14. The vacuum passageway 64 widens to accommodate a ball valve 66 that is biased to open in response to application of a vacuum by the vacuum pump 12. The ball valve 66 includes a ball 68 that is normally held by a compression spring 70 in a position to block air flow.

The vacuum pump 12 is threadably attached to the body 14 (see FIG. 6). Components of the vacuum pump 12 are best illustrated in FIGS. 1, 3, and 6. The vacuum pump 12 includes a handle 90 attached to a shaft 88 that extends through a pump end wall 78 into piston interior 82 of a cylindrically configured piston wall 80. The shaft 88 connects to a piston 84 capable of reciprocating movement in the piston interior 82 between the pump end wall 78 and the body 14. A sliding piston seal 86 attached to the piston 84 maintains an airtight seal with the piston wall 80 as the piston 84 is reciprocated.

In operation, withdrawal of an oil sample from a non-pressurized oil source involves threaded attachment of external threads 54 on neck 52 of sample bottle 50 to internal threads 74 defined in the neck receptacle 72. Before threaded attachment of the sample bottle 50, a sealing ring 75 is positioned in the neck receptacle to provide a fluid tight seal. The rigid tube 22 is also sealed by insertion of the plug 18 into the tube interior 24. The proximal end 32 of the flexible tube 20 is then engaged with the coupling system 34 by passing the tube through passageway 38 of the compression nut 36, and through hole 42 of the elastic washer 40. The compression nut 36 is threaded onto external threads 46 of the stem 44, compressing the elastic washer 40 to provide a compression seal between the proximal end 32 of the flexible tube 20 and the elastic washer 40.

After the flexible tube 20 has been attached to the body 14 by the coupling system 34, the distal end 30 of the flexible tube 20 is inserted into a non-pressurized oil source (not shown). An operator of the oil sampling apparatus 10 grasps the handle 90 with one hand, and while holding the cylindrical piston wall 80 securely in the other hand (gripping ridges 92 help prevent slippage of the hand), moves the handle 90 outward from and toward the body 14. Since the handle 90 is connected to the piston 84 by the shaft 88, a vacuum is drawn in the vacuum passageway 64 on the outward stroke. In response to application of a vacuum, the ball 68 of the ball valve 66 moves against the spring 70 to allow a fluid connection between the vacuum passageway 64 and the conduit 60. The lowered pressure in the conduit 60 relative to the unpressurized oil source (maintained at normal atmospheric pressure) induces movement of oil through the flexible tube 20, into conduit 60 and neck receptacle 72, to drop into sample bottle 50. After the oil sample has been retrieved, the sample bottle 50 can be detached from the body 14, labelled, and stored for later analysis. Another sample bottle can be attached to the body 14 and the procedure repeated.

Taking oil samples from pressurized oil sources requires a different procedure. An operator removes the plug 18, and positions the rigid tube 22 in contact with a pressurized oil source. The rigid tube 22 is pushed forward into sealing contact with the pressurized oil source, simultaneously causing needle 26 to trigger release of oil from the oil source. Pressurized oil fills the tube interior 24 and passes through needle hole 28 of needle 26 to enter the pressurized oil passageway 62. The stream of oil enters the conduit 60, and passes downward into the sample bottle 50. After a sufficient amount of oil is collected in the sample bottle, the operator pulls the rigid tube 22 away from the oil source, breaking the connection between the oil source release trigger (not shown) and the needle 26, and causing oil flow to cease. The sample bottle can be removed, stored, and replaced as previously described.

Figure 7:
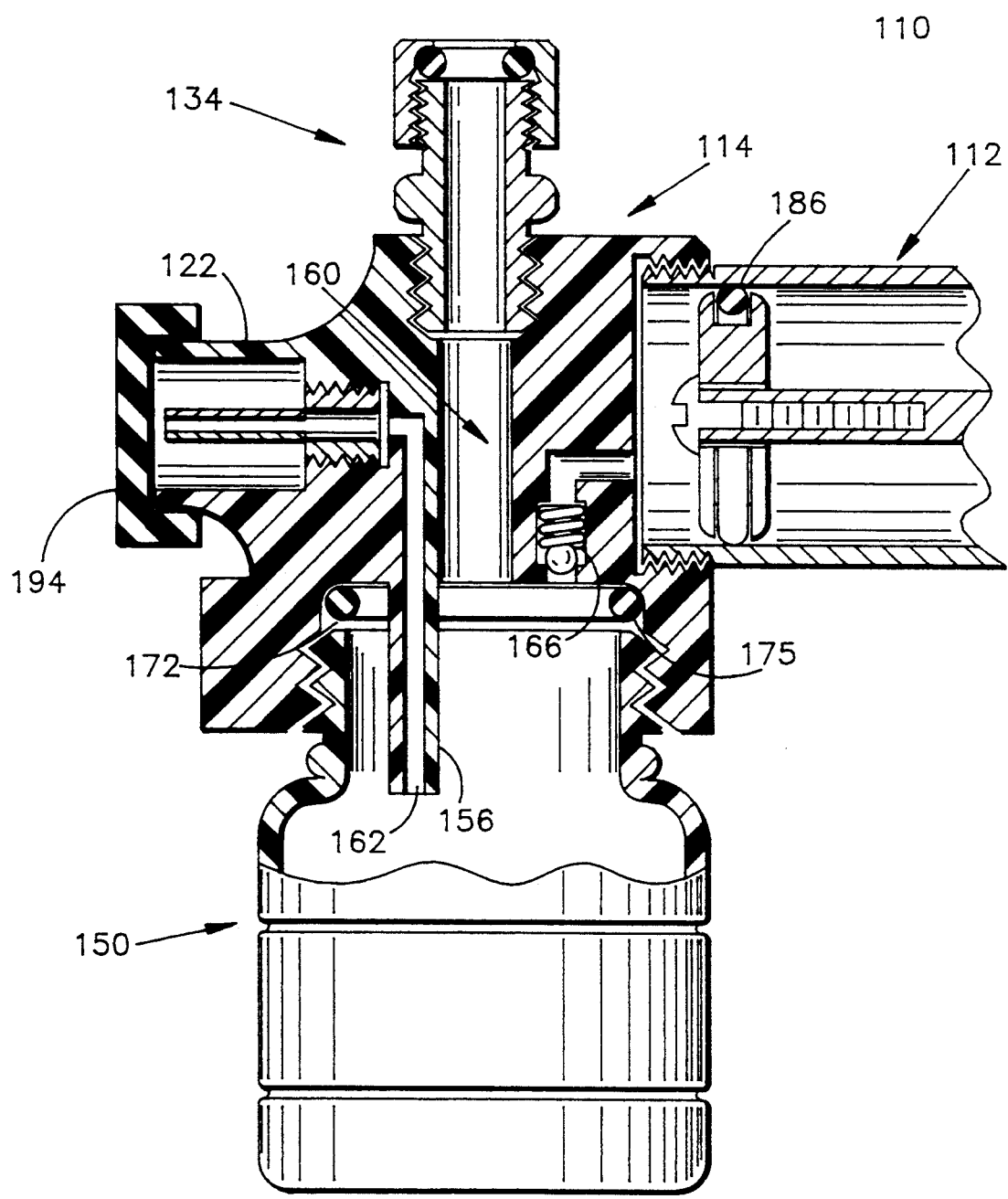
FIG. 7 is partial view of an alternative embodiment of a oil sampling apparatus with a body having a pressurized oil passageway that is downwardly directed toward a sample bottle.

An alternative embodiment of the invention is illustrated in FIG. 7. Corresponding numbers are intended to label parts substantially similar to labelled parts of FIG. 6 (e.g., body 14 of FIG. 6 substantially corresponds to body 114 of FIG. 7). The oil sampling apparatus 110 substantially corresponds to the embodiment illustrated in FIG. 6, with the exception of a replacement of a plug fitting into a tube interior by an airtight cap 194 that fits over the rigid tube 122 rather than inside like a plug. In addition, the positioning of pressurized oil passageway 162 slightly differs. Instead of joining in direct fluid communication with conduit 160, the pressurized oil passageway is downwardly directed to join in fluid communication with the neck receptacle 172 and sample bottle 150. To enhance effective movement of pressurized oil into sample bottle 150, the body 114 further defines a downward extension 156 that projects outlet of the pressurized oil passageway 162 toward the sample bottle 150.

Figure 8:
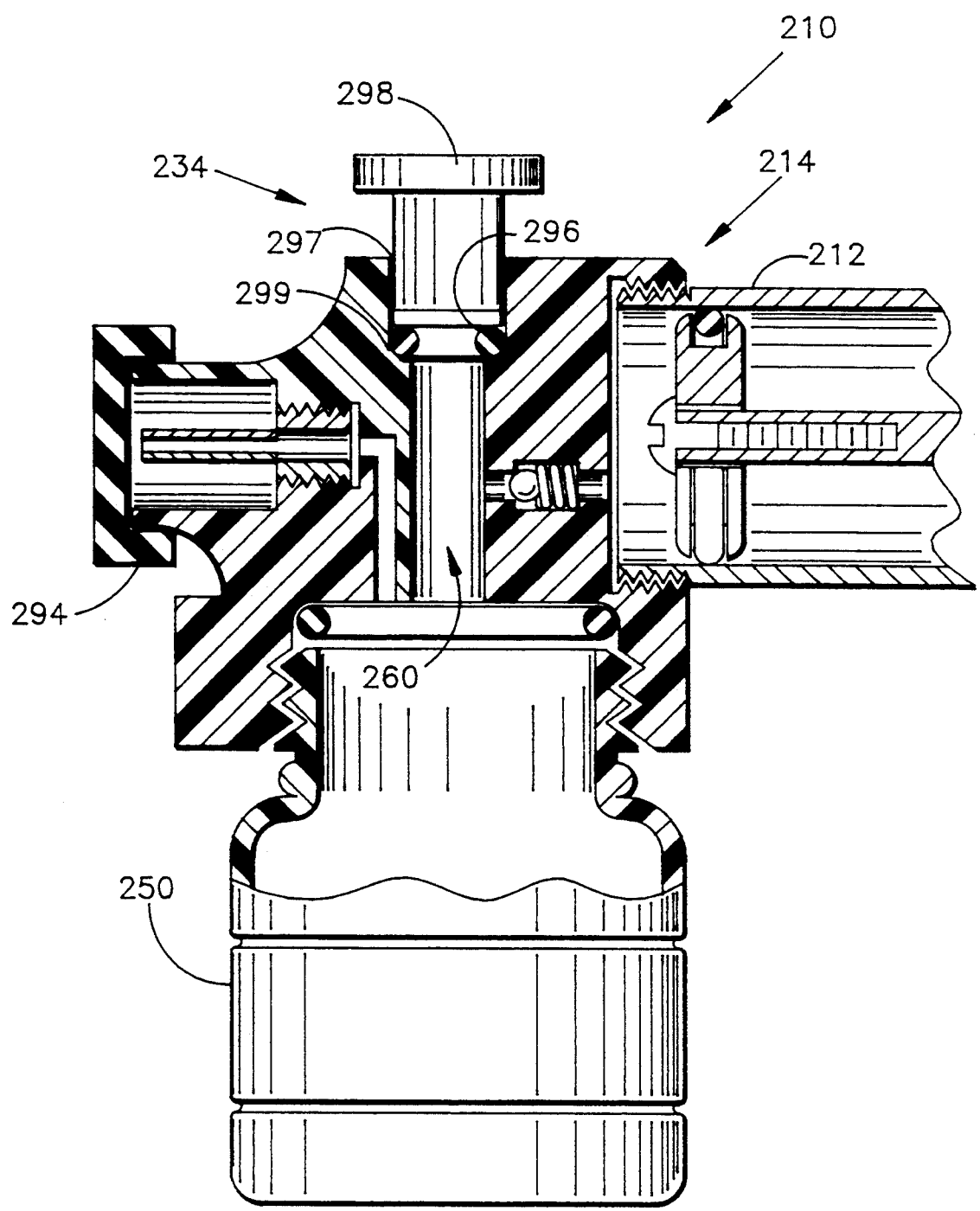
FIG. 8 is a partial view emphasizing a body of an alternative embodiment of an oil sampling apparatus, showing coupling system that includes a compression screw threadedly engagable with threads defined in a conduit defined to extend through the body.

Another alternative embodiment is illustrated in FIG. 8, which shows an oil sampling apparatus 210 having a coupling system 234 that differs from the previously described coupling system 34. Again, corresponding numbers are intended to label parts substantially similar to labelled parts of FIG. 6 and 8 (e.g., body 14 of FIG. 6 substantially corresponds to body 214 of FIG. 8, or cap 194 of FIG. 7 corresponds to cap 294 of FIG. 8). As illustrated, a compression screw 298 is threaded into a bore 297 defined in a body 214. The bore 297 terminates at a bevel 299 defined at the junction between the bore 297 and a conduit 260. An 0-ring 296 rests on the bore 297. A flexible tube (not shown) can be positioned to pass through the bore 297. When the compression screw 298 is screwed into the bore, the 0-ring is compressed and expands to contact and seal the flexible tube. With the exception of the coupling system, operation of this embodiment is otherwise similar to the embodiment described in connection with FIGS. 1–6 and 7.

The claimed invention is:
1. An oil sampling apparatus for taking samples form either pressurized or non-pressurized oil sources, the apparatus comprising
   a body having an upper and a lower side, the body being configured to define an conduit therethrough extending between the upper and lower sides, a neck recepticale define adjacent to said lower side in fluid communication with the conduit, a vacuum passageway defined to extend through the body in direct fluid communication with the neck receptacle, a pressurized oil passageway defined to extend through the body in fluid communication with the conduit, and the body further defining a right tube having a tube interior connectable between a source of pressurized oil and the pressurized oil passageway,
   a sample bottle positionable adjacent to the lower side of the body in fluid tight communication with the the neck receptacle,
   a manually operated vacuum pump attached in fluid communication to the vacuum passageway,
   a needle positioned in the tube interior and configured to trigger release of pressurized oil from the source of pressurized oil when connected to the source of pressurized oil,
   a flexible tube insertible through the upper side of the body into the conduit for conveying oil between a non-pressurized oil source and the conduit, a coupling system attached to the upper side of the body to connect the flexible tube in fluid tight connection with the conduit, and a removable seal for removably sealing the tube interior to promote drawing a vacuum in the conduit when oil is drawn by action of the manually operated vacuum pump from a non-pressurized oil source through the flexible tubing into the conduit.

2. The apparatus of claim 1 wherein the needle is formed to define a needle hole therethrough, the needle hole being connected in fluid communication with the pressurized oil passageway to allow passage of pressurized oil from the tube interior, through the needle hole, and into the pressurized oil passageway.

3. The apparatus of claim 1 wherein the sample bottle is formed to define external threads engagable with internal threads defined in the body.

4. The apparatus of claim 1 wherein the coupling system includes a stem attached to the body in fluid communication with the conduit, the stem extending outward from the body and allowing insertion therethrough of the flexible tube, and a compression nut having a passageway therethrough to allow insertion therethrough of the flexible tube, with attachment of the compression nut to the stem compressing a compressible elastic washer positioned therebetween to hold the flexible tube in sealing engagment with the conduit of the body.

5. The apparatus of claim 1 wherein the coupling system further comprises a compressible seal positioned in the conduit and a compression screw having a passageway therethrough to allow insertion therethrough of the flexible tube, the compression screw extending downward into the conduit to compress the compressible seal and seal the flexible tube.

6. The apparatus of claim 1 wherein the sealing means further comprises a cap inserted over the rigid tube.

7. The apparatus of claim 1 wherein the sealing means further comprises a plug inserted into the tube interior of the rigid tube.

8. The apparatus of claim 1 wherein the body is formed to define a plurality of internal threads dimensioned to engage a plurality of external threads defined by the vacuum pump to hold the vacuum pump to the body.

9. The apparatus of claim 1 wherein the manually operated vacuum pump further comprises a piston positioned for reciprocating movement.

10. An oil sampling apparatus for taking an oil sample from either a pressurized or non-pressurized oil source and storing the oil sample in a removably attached sample bottle, the apparatus comprising a body formed to define a conduit therethrough, with the body defining a neck receptacle in fluid communication with the conduit, and the body further defining a vacuum passageway therethrough directly connected in fluid communication with the neck receptacle, and a pressurized oil passageway being defined to extend through the body in fluid communication with the conduit, means for attaching a sample bottle to the body in fluid communication with the conduit, a manually operated vacuum pump attached in fluid communication to the vacuum passageway, means for triggering release of pressurized oil from a pressurized oil source, wherein the triggering means is in fluid communication with the pressurized oil passageway, means for conveying oil between a non-pressurized il source and the conduit, means for coupling the conveying means in fluid tight connection with the conduit, and means for sealing the pressurized oil passageway to promote drawing a vacuum in the conduit when oil is drawn by action of the manually operated vacuum pump from a non-pressurized oil source through the conveying means into the conduit.

11. The apparatus of claim 10 wherein the triggering means further comprises a rigid tube integrally defined to project from the body, the rigid tube having a tube interior connectable between a source of pressurized oil and the pressurized oil passageway.

12. The apparatus of claim 11 further comprising a needle positioned in the tube interior, the needle being configured to trigger release of pressurized oil from the source of pressurized oil when connected to the source of pressurized oil 13. The apparatus of claim 12 wherein the needle is formed to define a needle hole therethrough, the needle hole being connected in fluid communication with the pressurized oil passageway to allow passage of pressurized oil from the tube interior, through the needle hole, and into the pressurized oil passageway.

14. The apparatus of claim 10 wherein the sample bottle is formed to define external threads engagable with internal threads defined in the body.

15. The apparatus of claim 10 wherein the conveying means further comprises a flexible tube having a proximal end positioned to extend into the conduit.

16. The apparatus of claim 10 wherein the means for coupling further comprises a stem attached to the body in fluid communication with the conduit, the stem extending outward from the body and allowing insertion therethrough of the conveying means, and a compression nut having a passageway therethrough to allow insertion therethrough of the conveying means, with attachment of the compression nut to the stem compressing a compressible elastic washer positioned therebetween to hold the conveying means in sealing engagment.

17. The apparatus of claim 10 wherein the coupling means further comprises a compressible seal positioned in the conduit and a compression screw having a passageway therethrough to allow insertion therethrough of the conveying means, the compression screw extending downward into the conduit to compress the compressible seal and seal the conveying means.

18. The apparatus of claim 11 wherein the sealing means further comprises a cap inserted over the rigid tube.

19. The apparatus of claim 11 wherein the sealing means further comprises a plug inserted into the tube interior of the rigid tube.

* * * * *